United States Patent
Tsuji et al.

(10) Patent No.: US 8,100,877 B2
(45) Date of Patent: Jan. 24, 2012

(54) ABSORBENT ARTICLE

(75) Inventors: Tomoko Tsuji, Kagawa (JP); Hirotomo Mukai, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 272 days.

(21) Appl. No.: 11/945,457

(22) Filed: Nov. 27, 2007

(65) Prior Publication Data

US 2008/0125741 A1 May 29, 2008

(30) Foreign Application Priority Data

Nov. 27, 2006 (JP) ................................. 2006-319393

(51) Int. Cl.
*A61F 13/15* (2006.01)
*A61F 13/20* (2006.01)

(52) U.S. Cl. .......... 604/385.27; 604/385.25; 604/385.29

(58) Field of Classification Search ............. 604/385.01, 604/385.21–385.3, 394–396; 2/400–408
See application file for complete search history.

(56) References Cited

U.S. PATENT DOCUMENTS

| | | | | |
|---|---|---|---|---|
| 4,205,679 A | * | 6/1980 | Repke et al. | 604/366 |
| 4,743,241 A | * | 5/1988 | Igaue et al. | 604/385.26 |
| 5,745,922 A | * | 5/1998 | Rajala et al. | 2/243.1 |
| 6,049,916 A | * | 4/2000 | Rajala et al. | 2/400 |
| 6,340,569 B1 | * | 1/2002 | Ball et al. | 435/7.2 |
| 2004/0225270 A1 | * | 11/2004 | Hermansson et al. | 604/385.01 |

FOREIGN PATENT DOCUMENTS

| | | | |
|---|---|---|---|
| JP | 06090979 | | 4/1994 |
| JP | 11107007 A | * | 4/1999 |
| JP | 2001522703 | | 11/2001 |
| JP | 2004105704 A | * | 4/2004 |
| JP | 2004236832 | | 8/2004 |
| JP | 2006-061682 | | 3/2006 |
| JP | 2006-346439 | | 12/2006 |
| JP | 2007-044165 | | 2/2007 |
| JP | 2007-330543 | | 12/2007 |
| WO | WO-9925296 | | 5/1999 |
| WO | WO 2004078082 A1 | * | 9/2004 |

* cited by examiner

*Primary Examiner* — Melanie Hand

(74) *Attorney, Agent, or Firm* — Morrison & Foerster LLP

(57) ABSTRACT

An absorbent article including a chassis having a front body and a back body with a waist opening and leg openings, and an absorbent body of higher stiffness than that of the chassis. The front body and the back body consist of a composite sheet stretchable in the width direction WD. A line DL and a line CL2' form an angle in the range of 0 to 50 degrees. DL is a line connecting a bottom-most point PI on the connection between the front body and back body edge portions, and point P2 where the back body meets a crotch portion. CL2' is a line in the transverse direction of the article which passes through the end point P2.

4 Claims, 6 Drawing Sheets

ABSORBENT ARTICLE

This application is based on and claims the benefit of priority from Japanese Patent Application No. 2006-319393, filed on Nov. 27, 2006, the content of which is incorporated herein by reference.

BACKGROUND OF THE INVENTION

1. Field of the Invention

The present invention relates to absorbent articles such as disposable diapers.

2. Related Art

Conventional disposable diapers could be easily displaced by leg movement and the like. Such a displacement leads to leakage of the discharged matter.

In contrast, a disposable diaper is proposed in Japanese Unexamined Patent Application Publication No. 2006-61682 (hereinafter referred to as "Patent Document 1") which is aimed at inhibiting the displacement by shaping a diaper body to follow a wearer's body shape and bone structure. Specifically, in the developed state, a front flap and a rear flap in the lengthwise direction are arranged so that a distance between the lower ends thereof is in the range of 210 to 280 mm, and the width of the narrowest part at the vicinity of the longitudinal direction center of the diaper is in the range of 50 to 160 mm.

However, the disposable diaper disclosed in Patent Document 1 merely has a shorter and narrower crotch, and does not address the displacement of a disposable diaper. Particularly, the gap and waviness due to the difference in stiffness between absorbent article and chassis is not addressed at all in the disposable diaper of Patent Document 1.

SUMMARY OF THE INVENTION

The objective of the present invention is to provide an absorbent article such as disposable diaper which can inhibit a displacement during wearing.

In a first aspect of the present invention, an absorbent article includes: a chassis having a front body and a back body with an edge of a waist opening in a first direction and a crotch arranged therebetween, binding portions at both edges of the front body and the back body arranged in a second direction orthogonal to the first direction, an absorbent body which is arranged along the crotch to the back body, and a pair of leg openings composed of a pair of edges of front body and a pair of edges of the back body, in which the front body and the back body are composed of a stretchable composite sheet which is stretchable to the first direction obtained by binding a stretchable sheet and a non-stretchable sheet at a plurality of binding portions, and an angle between a line connecting a first lowest point which is the crotch-side end of the back body binding portion and a second lowest point which is the crotch-side end of the composite sheet on the edge of the back body, and an extended line of the crotch-side end of the composite sheet forming the back sheet, is in the range of 0 to 50 degrees.

In a second aspect of the absorbent article as described in the first aspect of the present invention, the absorbent article has a center line equally dividing the absorbent article in the lengthwise direction and includes stretchable members arranged along the edge of the leg openings at least in the back body, in which a minimal distance between the second lowest point of the back body and the center line is shorter than a minimal distance between a third lowest point which is the crotch-side end of the composite sheet on the edge of the front body and the center line.

In a third aspect of the absorbent article as described in the first or second aspect of the present invention, a length of the crotch in the second direction is in the range of 15 to 40% of that of the absorbent article in the second direction.

In a fourth aspect of the absorbent article as described in any one of the first to third aspects of the present invention, the side edges of the front body forming the leg openings are U-shaped having a projecting portion toward the end of the front body to the lengthwise direction.

In a fifth aspect of the absorbent article as described in any one of the first to fourth aspects of the present invention, during wearing, the most projecting portion of the leg openings toward the waist opening is arranged on the front body side.

Thus, the present invention can provide an absorbent article such as disposable diaper which can inhibit displacement during wearing. In addition, the present invention can provide an absorbent article such as a disposable diaper inhibiting displacement during wearing to prevent leakage of a discharged matter.

DETAILED DESCRIPTION OF THE INVENTION

Embodiments of the present invention are described below with reference to the accompanying drawings. However, it is to be understood that the embodiments of the present invention are not limited to the following, and the technical scope of the present invention is not limited thereto.

In this embodiment, a description is provided regarding the shorts-type disposable diaper including a waist opening and a pair of leg openings obtained by joining the front body and the back body at the binding portions. However, the present invention is not limited thereto. The present invention is also applicable to other uses, for example, as an expansion type disposable diaper which can be put on by engaging the front body and the rear body with an engaging member, etc. Alternatively, an engaging member such as a surface fastener used in the expansion-type disposable diaper may be disposed at the predetermined binding portion in the front body and the rear body of the shorts-type disposable diaper. This provides a disposable diaper of a pants-type that can be expanded and reengaged by easy release and engagement.

Figure 1:
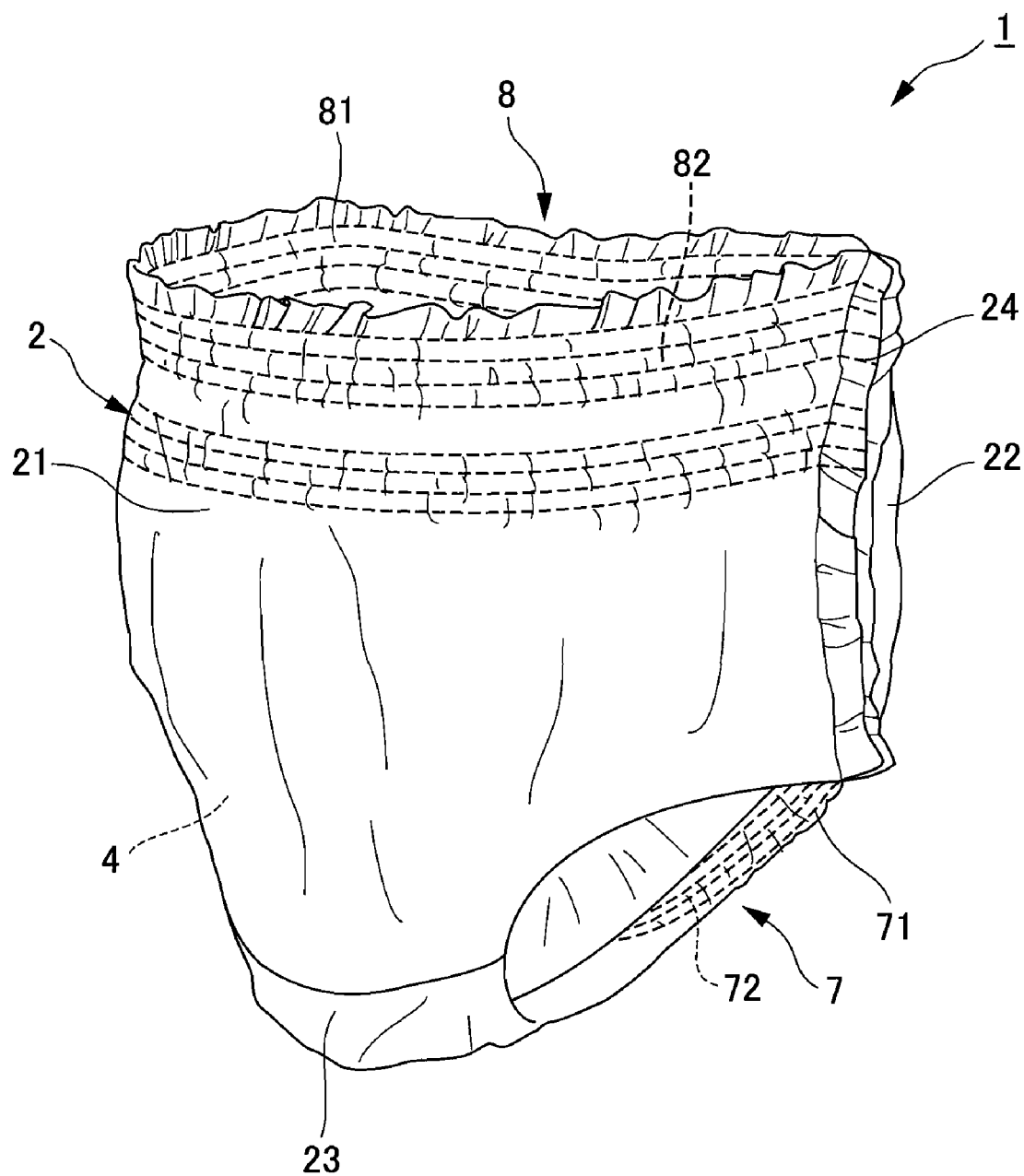
FIG. 1 is a perspective view showing a disposable diaper in the first embodiment of the present invention.
Figure 2:
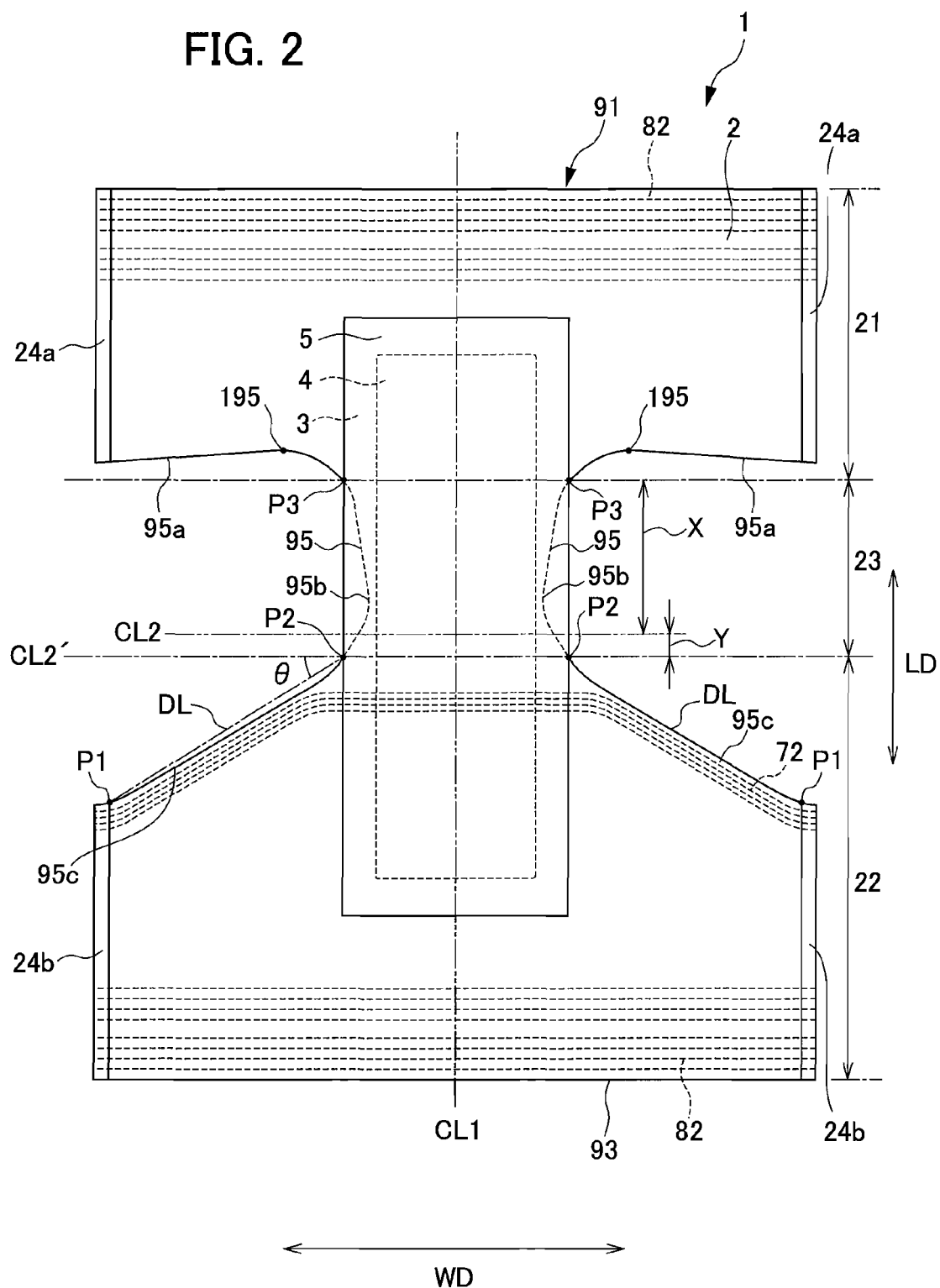
FIG. 2 is a top view showing the disposable diaper of FIG. 1 in the developed state.
Figure 3:
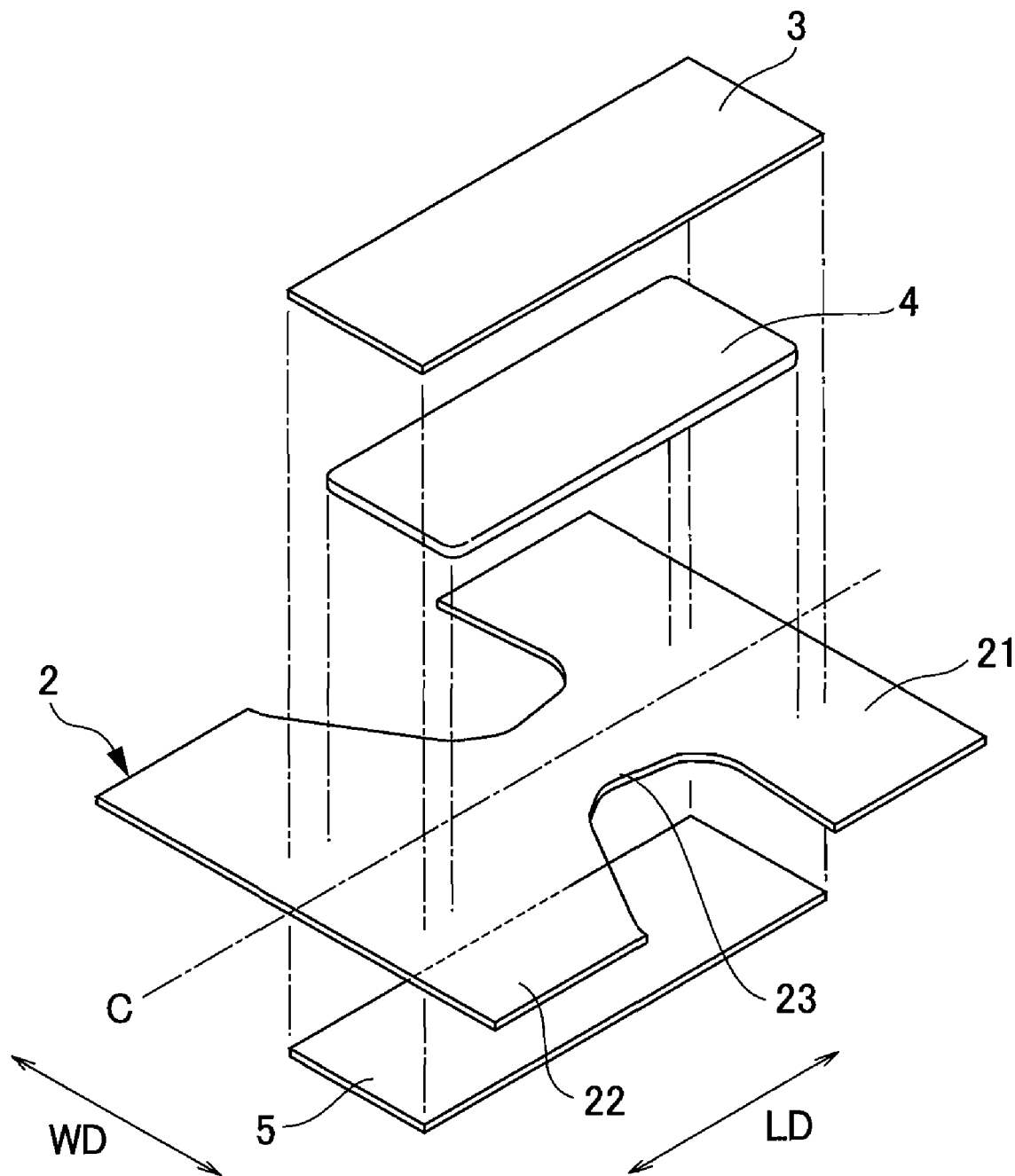
FIG. 3 is an exploded perspective view showing the disposable diaper of FIG. 1.

FIG. 1 is a perspective view showing a disposable diaper in the first embodiment of the present invention. FIG. 2 is a top view showing the disposable diaper of FIG. 1 in the developed state. FIG. 3 is an exploded perspective view showing the disposable diaper of FIG. 1.

1. Embodiment

1-1. General Configuration

The general configuration of the disposable diaper of the present invention will be described with regard to a disposable diaper 1 in the present embodiment. In the present embodiment, it is assumed that the side of the disposable diaper facing a wearer's body is a skin-contacting side, and the side opposite the skin-contacting side is a skin non-contacting side. It is also assumed that a width direction WD of a disposable diaper in the developed state is an example of the first direction, and a lengthwise direction LD is an example of the second direction, which intersects with the first direction.

As shown in FIG. 1 and FIG. 2, the disposable diaper 1 according to the present embodiment has a chassis 2 forming the outer body and waistline of the disposable diaper 1 during wearing. The chassis 2 includes a front body 2-1 facing a wearer's abdomen having an edge of a waist opening 8 in a width direction WD, a back body 22 facing a wearer's back having an edge of a waist opening 8 in the width direction WD and a crotch 23 arranged therebetween.

As shown in FIG. 2, the crotch 23 is narrower in width than the front body 21 and the back body 22, and the front body 21 and the back body 22 also have a narrowed area neighboring to the crotch 23. Additionally, the disposable diaper 1 is formed so that upper and lower ends (to the length direction) are wider and a central portion to the length direction is narrower. In other words, the disposable diaper 1 (the chassis 2) is shaped like an hourglass.

As shown in FIG. 1, the disposable diaper 1 includes a predetermined binding portion 24 on both sides of the front and back bodies along the lengthwise direction. The disposable diaper 1 is formed in a so-called shorts-shape by superimposing and joining the front body 21 and the back body 22 at the binding portion 24.

Specifically, the disposable diaper 1 is formed in a shorts-shape as shown in FIG. 1 by laminating a binding portion 24*a* of the front body 21 and a binding portion 24*b* of the back body as shown in FIG. 2. In other words, a pair of edges 95 becomes a pair of leg openings 7. Moreover, an edge along the width direction (a front edge 91 and a back edge 93) WD becomes a waist opening 8.

The edge of the leg openings 7 may be arranged with a predetermined elastic member in its entirety or in part. The elastic member is an example of a stretchable member arranged, at least in the back body 22, along the edge of the leg openings 7. Specifically, as shown in FIG. 2, a plurality of filiform or band-shaped elastic members 72 can be arranged along edges 95*c* in the back body 22. Leg gathers 71 as shown in FIG. 1 are thus provided.

Similarly, the edge of the waist opening 8 may be arranged with a predetermined elastic member. Specifically, as shown in FIG. 2, a plurality of filiform or band-shaped elastic members 82 can be arranged along the front edge 91 in the front body 21, and a plurality of filiform or band-shaped elastic members 82 can be arranged along the back edge 93 in the back body 22. Waist gathers 81, as shown in FIG. 1, are thus provided.

As shown in FIG. 3, the disposable diaper 1 includes a vertically long liquid permeable surface sheet 3 disposed on the skin-contacting side constituting a surface layer, a vertically long liquid retentive absorbent body 4 disposed between the surface sheet 3 and the chassis 2 constituting an absorbent layer, and a vertically long liquid impermeable back sheet 5 disposed on the skin non-contacting side constituting a back layer. The surface sheet 3, the absorbent body 4, and the back sheet 5 are placed in the lengthwise direction from the front body 21 through the back body 22 via the crotch 23. Thus, discharged matter from the excretory part, such as urine, passes through a liquid permeable region of the surface sheet 3, and is then absorbed by the absorbent body 4. Since the back sheet 5 disposed on the skin non-contacting side is liquid impermeable, the discharged matter such as urine can be absorbed by the absorbent body 4 and retained as is, without reaching the skin non-contacting surface. The surface sheet 3 or the back sheet 5 is an example of a sheet member covering at least one side of the absorbent body 4 according to the present invention.

1-2. Chassis

As shown in FIGS. 1 and 2, the chassis 2 includes the front body 21 facing a wearer's abdomen during wearing, the back body 22 facing a wearer's back, and the crotch 23 arranged therebetween. The front body 21, the crotch 23, and the back body 22 are arranged in this order from one end to the lengthwise direction LD.

The length of the chassis 2 in the lengthwise direction LD is preferably in the range of 650 to 800 mm, and the length thereof in the width direction WD is preferably in the range of 450 to 900 mm. In addition, the length of the front body 21 in the lengthwise direction LD is preferably in the range of 185 to 285 mm, and length of the outer portion (a front edge 91) thereof in the widthwise direction WD is preferably in the range of 450 to 900 mm. The length of the back body 22 in the lengthwise direction LD is preferably in the range of 285 to 385 mm, and the length of the outer portion (a rear edge 93) thereof in the widthwise direction WD is preferably in the range of 450 to 900 mm.

The length of the crotch 23 in the lengthwise direction LD is preferably in the range of 130 to 230 mm, and length thereof in the width direction WD is preferably in the range of 100 to 200 mm. Moreover, the length of the crotch 23 in the lengthwise direction LD is in the range of 15 to 40% of that of chassis 2 in the lengthwise direction LD.

The front body 21 and the back body 22 of the chassis 2 are formed of a stretchable non-woven fabric which is stretchable to the width direction WD. Specifically, the front body 21 and the back body 22 are composite sheets obtained by laminating (binding) a stretchable non-woven fabric and a non-stretchable non-woven fabric, and are formed of composite sheets obtained by binding a stretchable non-woven fabric in an expanded state and a non-stretchable non-woven fabric at regular intervals in the predetermined stretching direction of the stretchable sheet. In other words, in the configuration according to the present invention, the front body 21 and the back body 22 are composed of stretchable composite sheets obtained by binding a stretchable non-woven sheet and a non-stretchable non-woven sheet of a stretchability different therefrom, at a plurality of binding portions. The weight of the composite sheet in a natural state (non-expanded state) is in the range of 30 to 230 g/m$^2$, and the sum of the weight of all the non-woven fabrics and sheets (in a non-bound state) is in the range of 30 to 130 g/m$^2$.

The edges 95(*a-c*) and 95(*a-c*) are U-shaped portions projecting inward toward a centerline CL1 in the width direction WD. The edges 95(*a-c*) and 95(*a-c*) are composed of 95*a* and 95*a* arranged in the front body 21, 95*b* arranged in the crotch 23, and 95*c* and 95*c* arranged in the back body 22. The edges 95(*a-c*) and 95(*a-c*) form a pair of leg openings 7 during wearing.

The edges 95*a* are gently U-shaped and projecting toward a front edge of the front body 21 in the lengthwise direction.

Figure 5:
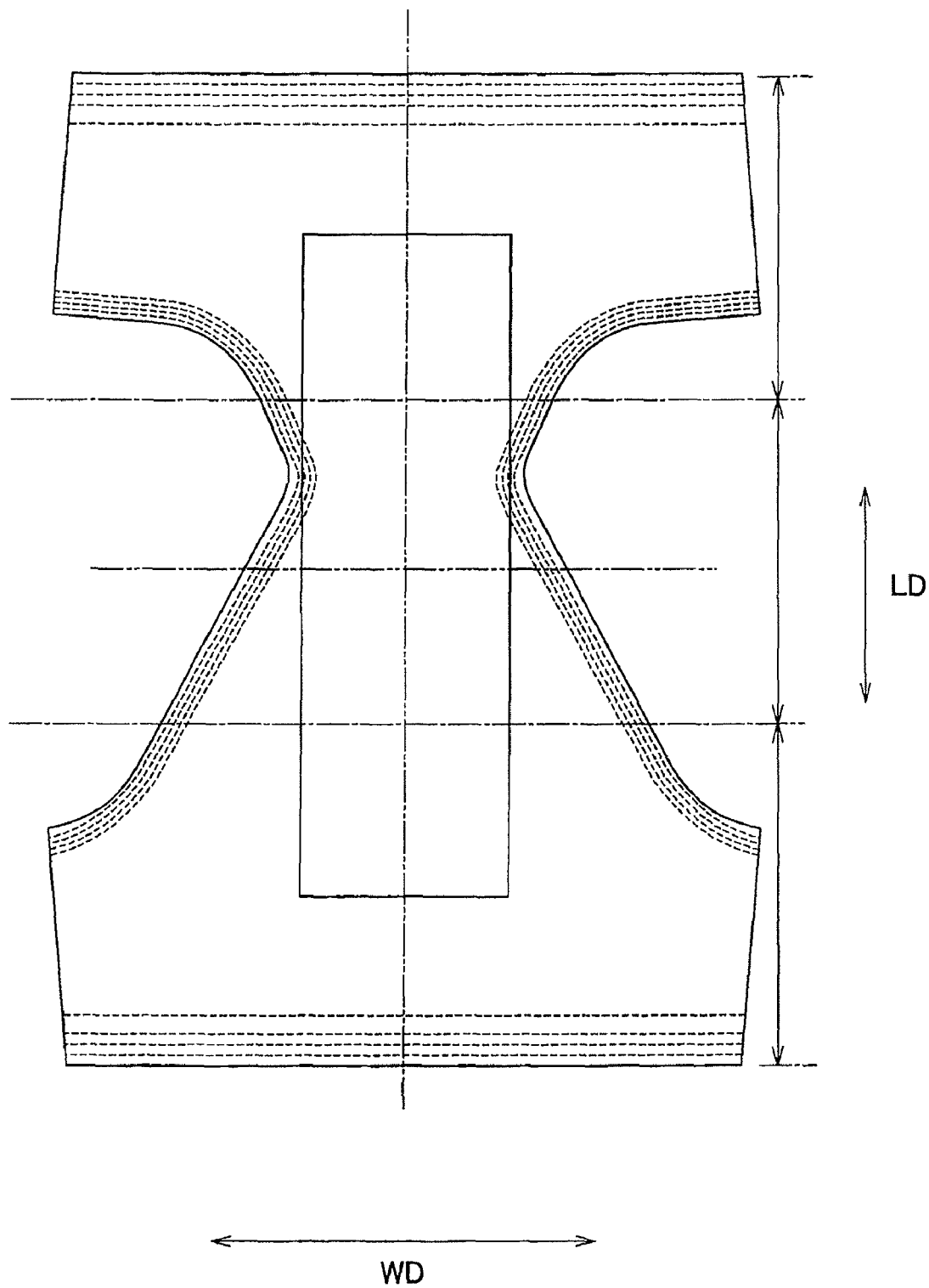
FIG. 5 is a top view showing a conventional disposable diaper.
Figure 6:
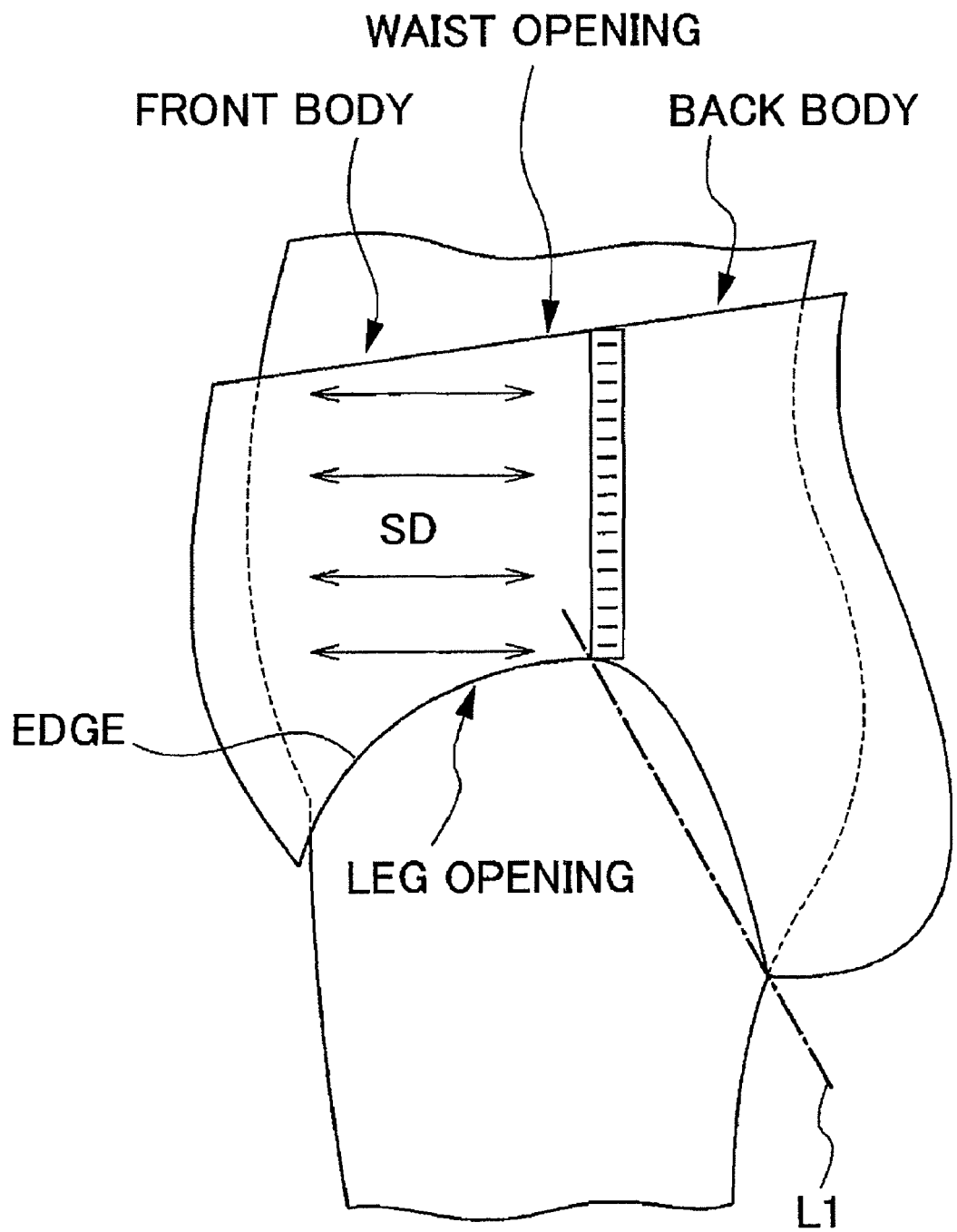
FIG. 6 is a side view illustrating the configuration when wearing the conventional disposable diaper.

In other words, the edges 95*a* are projecting toward the edge of the waist opening 8 as approaching a back sheet 5 (195 in the U-shaped portion 95 of FIG. 2). As shown in FIG. 5, in a front body of a conventional disposable diaper, the peak of an edge (a part of a leg opening) in the lengthwise direction LD is in outermost portion of the width. In contrast, in 95*a* of the disposable diaper of the present invention, the peak in the lengthwise direction LD is 195. In other words, leg openings of the present invention are projecting toward the waist opening 8.

Edges 95*b* formed on the crotch 23 are arranged as part of the edges 95 of chassis 2 and inside an edge formed from liquid-impermeable back sheet 5.

Edges 95*c* in the back body 22 are lines extending outward in the width direction WD as approaching the waist opening (outward in the lengthwise direction). For example, regarding an arbitrary edge 95*c*, a line DL and a line CL2' form an angle which is in the range of 0 to 50 degrees, and more preferably 20 to 40 degrees. Here, DL is a line connecting the lowest point P1 (a first lowest point according to the present invention) of the binding portion 24 in the back body 22 with an end point P2 (a second lowest point according to the present invention) of the stretchable portion (a border between the back body composite sheet 22 and the crotch 23); and CL2' is an extended line of an end of a composite sheet forming the back body 22 which passes through the end point P2. When the angle θ is in the abovementioned range, an angle θ' is also in the preferred range of 0 to 50 degrees, and more preferably 20 to 40 degrees. Here, θ' is an angle of the edges 95*c* constituting the leg openings 7 with respect to the waist direction, more specifically while referring to FIGS. 4A and 4B, an angle of a line L1 with respect to a stretching direction SD which provides a superior stretchability during wearing.

As shown in FIG. 2, the chassis 2 is formed so that a distance Y between CL2 and P2 is shorter than a distance X between CL2 and P3 (a third lowest point according to the present invention). Here, CL2 is a centerline equally dividing the absorbent article 1 in the lengthwise direction LD; P2 is the abovementioned end point; and P3 is an end point of the stretchable portion (a border between the front body composite sheet 21 and the crotch 23). In addition, a distance from a front intersection of the stretchable member 82 and CL1 to CL2 and a distance from a rear intersection of 82 and CL1 to CL2 show, for example, a ratio in the range of 65:35 to 85:15. Thus, the edges 95*c* in the back body 22 fit from an inner part to an outer part of the thighs during wearing.

Furthermore, an elastic member 72 is arranged from an edge 95*c* to the other edge 95*c* in the width direction WD, as shown in FIG. 2. Specifically, the elastic member 72 is arranged along each of the edges 95*c* of leg openings 7 and parallel to the width direction WD connecting both of the inner sides (to the width direction) of the edges 95*c*. The elastic members 72 arranged along the edges 95*c* form leg gathers 71 on the leg openings 7, and inhibit displacement of the back body 22 during wearing. The elastic member 72 may be either filiform or band-shaped. A band-shaped elastic member includes a stretchable non-woven fabric such as a non-woven fabric made of a mixed fabric of polyurethane and polypropylene, and an elastic sheet such as a stretchable film.

In addition, as shown in FIG. 2, a plurality of elastic member 82 is arranged along a front edge 91 and a rear edge 93 of the waist opening 8. These elastic members 82 form a waist gather 81 on the waist opening 8 and inhibit downward displacement of the disposable diaper 1 during wearing. The elastic members 82 may be band-shaped. The elastic member 82 includes a stretchable non-woven fabric such as a non-woven fabric made of a mixed fabric of polyurethane and polypropylene, and an elastic sheet such as a stretchable film.

As shown in FIG. 2, the chassis 2 includes binding portions 24*a* and binding portions 24*b* on both ends in the width direction WD of the front body 21 and back body 22 along the lengthwise direction LD. The front body 21 and the back body 22 are joined by joining the binding portions 24*a* on the front body 21 with the binding portions 24*b* on the back body 21 by ultrasonic sealing. The chassis 2 is thus formed in a shorts-shape as shown in FIG. 1. An example of a joining method at the binding portion 24 includes hot sealing or joining by a hot-melt adhesive.

1-3. Absorbent Body

The absorbent body 4 is liquid retentive and formed in a substantially elongated shape. It should be noted that the wording "substantially elongated" includes a generally rectangular shape having a longitudinal direction and a width direction. Moreover, the wording includes a shape in which a portion of both sides in the longitudinal direction is tapered to the center in the longitudinal direction or bulged in the direction opposite the center. Specifically, the absorbent body 4 includes an absorbent body that is different in length in the width direction in a portion in the longitudinal direction.

The absorbent body 4 may be arranged in a state of being covered with tissues (not shown) or a hydrophilic non-woven fabric (not shown). When covered with a hydrophilic non-woven fabric, the absorber 4 may be configured without application of the surface sheet 3 or with only partial application thereof. This allows for a reduction in manufacturing cost.

In addition, stiffness of the absorbent body 4 is higher than that of a stretchable composite sheet constituting chassis 2. In other words, stiffness of a composite sheet arranged in the vicinity of the absorbent body 4 is lower than that of the absorbent body 4. Conventionally, in a case in which stiffness is different between the chassis 2 and the absorbent article 4, a predetermined area of the chassis 2 arranged in the vicinity of the absorbent body 4 could produce a gap between the chassis 2 and a wearer's body due to deformation of the absorbent body 4. The disposable diaper 1 of the present embodiment inhibits such a gap from developing by the abovementioned arrangement.

1-4. Others

The liquid-permeable surface sheet 3 and the absorbent body 4 are adhesively joined with a hot-melt adhesive. The surface sheet 3 and the absorbent body 4 are also adhesively joined to the chassis 2 with the hot-melt adhesive. Similarly, the chassis 2 and the liquid-impermeable back sheet 5 are adhesively joined with the hot-melt adhesive.

1-5. Configuration During Wearing

Figure 4A:
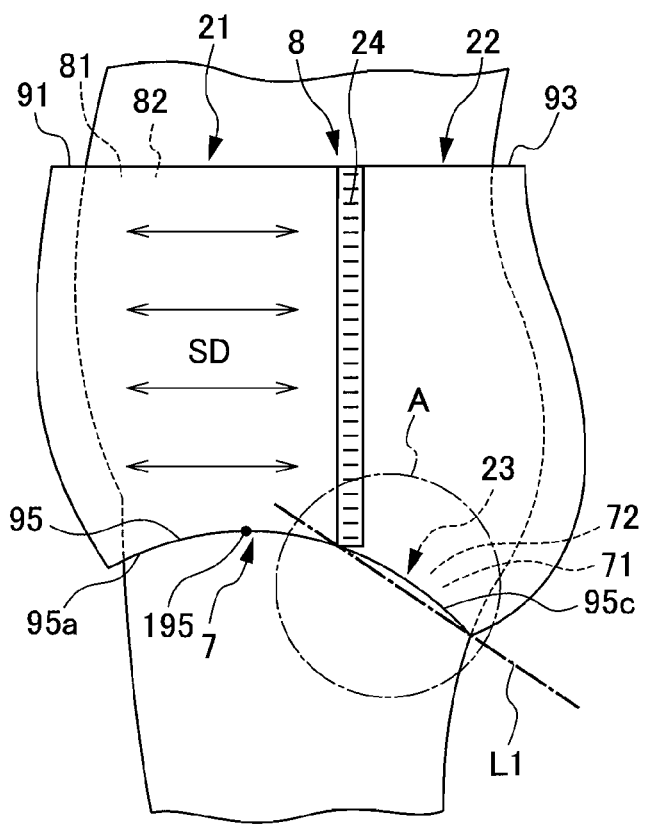
FIG. 4A is a side view illustrating the configuration when wearing the disposable diaper of FIG. 1.
Figure 4B:
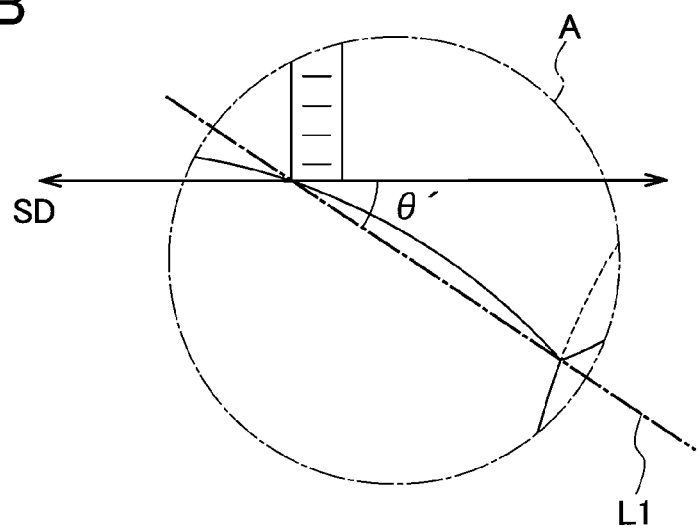
FIG. 4B is an enlarged view of a region A of FIG. 4A.

The configuration of the disposable diaper 1 during wearing is described hereafter. As shown in FIGS. 1, 4A, and 4B, the disposable diaper 1 includes a waist opening 8 composed of a front edge 91 and a rear edge 93, and a pair of leg openings 7 composed of a pair of edges 95 in an opposite side from the waist opening. In other words, the pair of leg openings 7 is composed of edges of the front and rear body with the exception of a pair of binding portions 24*a* and a pair of binding portions 24*b*.

A front body 21 and a back body 22 have a superior stretchability in a waist direction, since the front body 21 and the back body 22 are composed of a stretchable composite sheet. A waist gather 81 composed of a plurality of elastic members 82 is arranged in a waist opening 8 and a leg gather 71 composed of a plurality of elastic members 72 is arranged in each of the leg openings 7. The waist gather 81 and the leg gather 71 are arranged to squeeze appropriately a wearer's waist and legs.

By the presence of the front body 21 and back body 22 stretching in the waist direction, the waist gather 81, and the leg gathers 71, the disposable diaper 1 deforms and adheres to a wearer's body and inhibits displacement due to leg movement and the like. Here, the abovementioned gap occurring due to the difference in stiffness between an absorbent article 4 and a chassis 2 still needs to be addressed. Specifically, a gap and waviness occurring along a wearer's buttocks and legs during wearing (the lower part of the back body 22), which may cause leakage of a discharged matter, are particularly undesirable.

As shown in FIGS. 4A and 4B, an angle θ' of the edge 95c with respect to the waist direction (stretching direction) of the disposable diaper 1 is about 30 degrees. Here, the edge 95c is an outer edge of the back body 22 constituting a leg opening 7. The angle with respect to the stretching direction, θ', of the disposable diaper 1 of the present embodiment is lower than that of conventional disposable diapers. In other words, an edge 95 of the leg opening 7 is arranged to appear as a nearly horizontal line during wearing. If the angle θ' is in the abovementioned range, the stretching (contracting) force of the front body 21 pulls up a lower part of the back body 22 appropriately. In addition, the front body 21 stretching in the waist direction, the leg gathers arranged on the back body side of leg openings 7, and a plurality of elastic members constituting the leg gathers 71 pull at each other and inhibit the displacement at the lower part of the back body 22.

The most projecting portions 195 of the leg openings 7 toward the waist opening 8 are arranged in the front body 21 side. In such a configuration, the stretching (contracting) force of the front body 21 pulls up a lower portion of the back body 22 more appropriately.

The disposable diaper 1 of the present embodiment can inhibit the development of a gap due to the difference of stiffness between the absorbent body 4 and the chassis 2. Leakage of discharged matter due to the abovementioned gap is thus inhibited.

Although not arranged in the present embodiment, elastic members can obviously be arranged in the edges 95a of the leg openings 7 of the front body 21. In a case in which elastic members are arranged along the edges 95a on the front body side, a plurality of elastic members 72 arranged in the edges 95c of the back body 22, in addition to the front body 21 itself, also pulls at the elastic members of 95a, and inhibits more appropriately a displacement at the lower portion of the back body 22.

The angle θ' may be measured in a state in which an intended wearer wears the disposable diaper 1. The angle θ' may also be measured in a state in which a cylindrical column of an appropriate diameter is inserted through a leg opening 7 so that the leg opening 7 is expanded to an assumed degree of expansion during wearing (for example, 120%).

The disposable diaper 1 of the present embodiment can inhibit the occurrence of a gap and the like due to the difference of stiffness between the absorbent article 4 and the chassis 2, specifically a gap and waviness occurring along a wearer's buttocks and legs during wearing (the lower part of the back body 22), and can inhibit leakage of discharged matter due thereto.

Moreover, comfort during wearing is thus improved.

In addition, an outline of the disposable diaper 1 is thus less visible on the clothes worn thereon.

It should be noted that, although the chassis 2 consists of the front body 21, the back body 22, and the crotch 23 in the present embodiment, the invention is not limited thereto. For example, a crotch 23 composed of other material can be arranged between the front body 21 and the back body 22 of the chassis 2. Without being limited thereto, the chassis 2 may include the front body 21 and the back body 22, in which the crotch having the surface sheet 3, absorbent body 4, and back sheet 5 may independently be joined to the chassis 2. In this alternative, the back sheet 5 and the chassis 2 may be joined at the crotch, and the back sheet 5 may be configured to play a role of the chassis 2.

Furthermore, in the present embodiment, the back sheet 5 is arranged by the skin non-contacting side of the wearer; however, it may arrange, for example, between the absorbent body 4 and the chassis 2 without being limited to this, when the chassis 2 is formed by a sheet member of framework of few sheets, it may be arranged between each of the sheet members of the framework. The back sheet 5 may include a back sheet having a non-woven fabric or the like joined to the skin non-contacting side. Joining a non-woven fabric or the like to the skin non-contacting side of the back sheet 5 is desirable in view of enhancement in a wearer's comfort during wearing, etc. A liquid-impermeable film is preferably applied to the back sheet 5 and unpreferable noises due to rubbing of the liquid-impermeable film, for example, can be prevented from occurring by joining a non-woven fabric or the like to the liquid-impermeable film.

2. Components

The components of the disposable diaper are described hereafter.

2-1. Chassis

Although the chassis 2 is composed of a composite sheet obtained by laminating 2 sheets in the disposable diaper 1 of the present embodiment, the chassis 2 can be composed of a single sheet. Preferably, the chassis 2 is made of a material having a strength that can resist damage even when undergoing a load due to compression, twist, friction, etc. during wearing and providing no stimulus to the skin, for example.

2-2. Surface Sheet The top sheet part 3, at the time of use, is disposed on the skin contacting side, and is also brought into contact with the excretory part. The surface sheet 3 may be liquid permeable over the entire surface or a portion thereof. The surface sheet 3 may be composed of either a single sheet-like member or a plurality of sheet-like members bonded together.

For the surface sheet 3, the abovementioned materials for the chassis 2 can be used.

2-3. Absorbent Body

Examples of the absorbent body 4 are a mixed laminate of a highly absorbent polymer and hydrophilic fibers, and a structure having a highly absorbent polymer fixed to hydrophilic sheets with a hot-melt adhesive, etc.

2-4. Elastic Member

Examples of the elastic members are members made of natural rubber or synthetic rubber such as styrene-butadiene, butadiene, isoprene or the like. An example of the sheet-like elastic member is a polyurethane foam having a basis weight of 30 g/m$^2$ to 80 g/m$^2$, and a non-woven fabric obtained from mixed fibers of polyurethane and polypropylene having a basis weight of 20 g/m$^2$ to 80 g/m$^2$.

2-5. Adhesive

As mentioned above, the surface sheet 3 and absorbent body 4 are adhesively joined to the chassis 2 with a hot-melt adhesive. The surface sheet 3 and the absorbent body 4 are adhesively joined with the hot-melt adhesive. Without being limited to hot-melt adhesion, joining may be made by heat-sealing, ultrasonic sealing, etc. alone or in combination.

What is claimed is:

1. An absorbent article comprising:
a chassis having a front body and a back body and a crotch portion arranged therebetween, the front body and the back body having an edge of a waist opening extending in a first direction,
side edge portions of the front body and the back body, respectively, being connected, the side edge portions extending in a second direction orthogonal to the first direction,
an absorbent body adjacent a skin-facing side of the chassis and extending from the front body, across the crotch portion and onto the back body,
a first sheet member covering a skin-facing side of the absorbent body, and
a pair of leg openings comprised of respective edges of the front body, the sheet member, and the back body,
stretchable members extending along back body portions of the leg openings and across a portion of the back body that is adjacent to the crotch portion;
wherein the front body and the back body each comprise a stretchable composite sheet which is stretchable in the first direction and which includes a stretchable sheet and a non-stretchable sheet connected at portions,
wherein each of the pair of leg openings includes a front edge portion formed by the front body, a crotch edge portion formed by the sheet member, and a back edge portion formed by the back body,
wherein the front edge portion of each of the pair of leg openings extends laterally inward from the connection between the side edge portions of the front body and the back body to a first connection point with the crotch edge portion, first approaching the waist opening and then diverging from the waist opening and toward the crotch edge portion,
wherein the crotch edge portion extends longitudinally from the front edge portion to a second connection point with the back edge portion,
wherein the back edge portion extends laterally outward from the crotch edge portion to a bottom-most point on the connection between the side edge portions of the front body and the back body, continually approaching the waist opening, and
wherein an angle is defined between a first line intersecting the second connection point and said bottom-most point on the connection between the side edge portions of the front body and the back body, and a second line extending along the first direction through the second connection point, which angle is in the range of 0 to 50 degrees.

2. The absorbent article according to claim 1 wherein a minimal distance between the second connection point and a lateral center line is shorter than a minimal distance between said first connection point and said lateral center line.

3. The absorbent article according to claim 1, wherein a length of the crotch in a longitudinal direction is in the range of 15 to 40% of a length of the chassis in the lateral direction.

4. The absorbent article according to claim 1, wherein the first sheet member comprises:
a liquid permeable sheet;
said absorbent article further comprising a liquid impermeable sheet disposed on a skin non-contacting side of the chassis and having length and width dimensions greater than length and width dimensions of said absorbent body.

* * * * *